United States Patent
Blake et al.

(10) Patent No.: US 11,688,508 B2
(45) Date of Patent: Jun. 27, 2023

(54) BIOMETRIC STATUS SENSING MEDIA THERAPY SYSTEM AND METHODS OF USE

(71) Applicant: Edgewater Safety Systems Inc., Saint Joseph, MI (US)

(72) Inventors: Richard R. Blake, Sawyer, MI (US); Zachary Paul Gordon, Berrien Springs, MI (US); Jeffery Banker, Petersburg, MI (US); Julie Anderson, Antioch, MI (US); Andrew Hayward, Baroda, MI (US); Ethan Hayward, Baroda, MI (US); Seth Vanderark, St. Joseph, MI (US)

(73) Assignee: Edgewater Safety Systems, Inc., Saint Joseph, MI (US)

( * ) Notice: Subject to any disclaimer, the term of this patent is extended or adjusted under 35 U.S.C. 154(b) by 211 days.

(21) Appl. No.: 17/011,303

(22) Filed: Sep. 3, 2020

(65) Prior Publication Data

US 2021/0065874 A1 Mar. 4, 2021

Related U.S. Application Data

(60) Provisional application No. 62/895,267, filed on Sep. 3, 2019.

(51) Int. Cl.
| | |
|---|---|
| *G16H 20/70* | (2018.01) |
| *G16H 40/67* | (2018.01) |
| *G06F 3/16* | (2006.01) |
| *G16H 10/60* | (2018.01) |
| *G16H 40/63* | (2018.01) |

(52) U.S. Cl.
CPC .............. *G16H 20/70* (2018.01); *G06F 3/167* (2013.01); *G16H 10/60* (2018.01); *G16H 40/63* (2018.01); *G16H 40/67* (2018.01)

(58) Field of Classification Search
CPC ........ G16H 20/70; G16H 40/67; G16H 10/60; G16H 40/63; G06F 3/167
See application file for complete search history.

(56) References Cited

U.S. PATENT DOCUMENTS

| | | | |
|---|---|---|---|
| 11,315,694 B2* | 4/2022 | Soenksen | G16H 50/30 |
| 2015/0154372 A1* | 6/2015 | Soenksen | G16H 50/30 |
| | | | 705/2 |
| 2016/0196104 A1 | 7/2016 | Gordon | |
| 2017/0238026 A1* | 8/2017 | Agrawal | H04N 21/25883 |
| | | | 725/14 |
| 2018/0220898 A1* | 8/2018 | Muehlbauer | A61B 5/7278 |
| 2020/0226549 A1* | 7/2020 | Singh | G06Q 10/1095 |
| 2021/0065696 A1* | 3/2021 | Bromand | G10L 25/84 |
| 2021/0065874 A1* | 3/2021 | Blake | G06F 3/165 |
| 2021/0313041 A1* | 10/2021 | Keene | G16H 40/67 |

* cited by examiner

*Primary Examiner* — David E Choi (74) *Attorney, Agent, or Firm* — Barnes & Thornburg LLP (57) ABSTRACT

A biometric status sensing media therapy system for the therapeutic care of a Consumer. The system has a media therapy device provided with a central processing unit, audio and/or visual input/output and wireless communications. The media therapy device is provided in wireless communication with a cloud computing and data storage resource. A collection of media files, transmitted to the media therapy device from the cloud computing and data storage resource for play by the media therapy device, is played by the media therapy device according to a pre-configured collection of rules based upon a time schedule and/or a biometric status of the consumer.

20 Claims, 8 Drawing Sheets

BIOMETRIC STATUS SENSING MEDIA THERAPY SYSTEM AND METHODS OF USE

CROSS-REFERENCE TO RELATED APPLICATION

This application claims the benefit of U.S. Provisional Application No. 62/895,267, titled: STATUS SENSING AUDIO THERAPY DEVICE AND METHODS OF USE, filed on 3 Sep. 2019, hereby incorporated by reference in its entirety.

BACKGROUND

Field of the Invention

This invention relates to a system and method of use for care of a consumer with mental disability, such as Dementia and/or Alzheimer's disease. More particularly, the invention relates to a system enabling cloud-based generation/collection of Consumer specific media files that can be played for the consumer according to a time schedule and/or specific local sensed event, such as distress of the consumer.

Description of Related Art

Diseases associated with memory-loss such as Alzheimer's and Dementia (AD) are a growing issue as the general population ages. Known therapies for AD include visual and/or audio repetition as memory feedback/reinforcement. Repeatedly manually generating these visual and/or audio stimuli for AD patients (Consumers) may consume significant Caregiver resources, increasing the overall cost of care.

Recent pandemic quarantine of elderly from the general population according to social distancing guidelines has further isolated Consumers from family members, increasing stress upon both Consumers and their family which in turn further increases the difficulty for Caregivers.

U.S. Patent Application Publication No. US2016/0196104 discloses a wearable programmable audio device that may be configured to play an audio file for the wearer according to a selected time schedule. The device requires manual audio file loading and play interval programming, which requires both significant Caregiver time and on-board switchgear which increases the device's size and cost.

Therefore, an object of the invention is to provide a system and method of use that overcomes deficiencies in the prior art.

BRIEF DESCRIPTION OF THE DRAWINGS

The accompanying drawings, which are incorporated in and constitute a part of this specification, illustrate embodiments of the invention, where like reference numbers in the drawing figures refer to the same feature or element and may not be described in detail for every drawing figure in which they appear and, together with a general description of the invention given above, and the detailed description of the embodiments given below, serve to explain the principles of the invention.

DETAILED DESCRIPTION

The inventors have recognized that improved usability and overall cost savings compared to the prior art are available via a wireless networkable device that is thereby remotely configurable. Utilizing cloud-based server and data mining techniques enables improved relevance of the selected media files. Further, the device may be configurable in real time, responsive to rules that may include audio and/or biometric sensing inputs, improving the efficacy of the media therapy provided.

Figure 1:
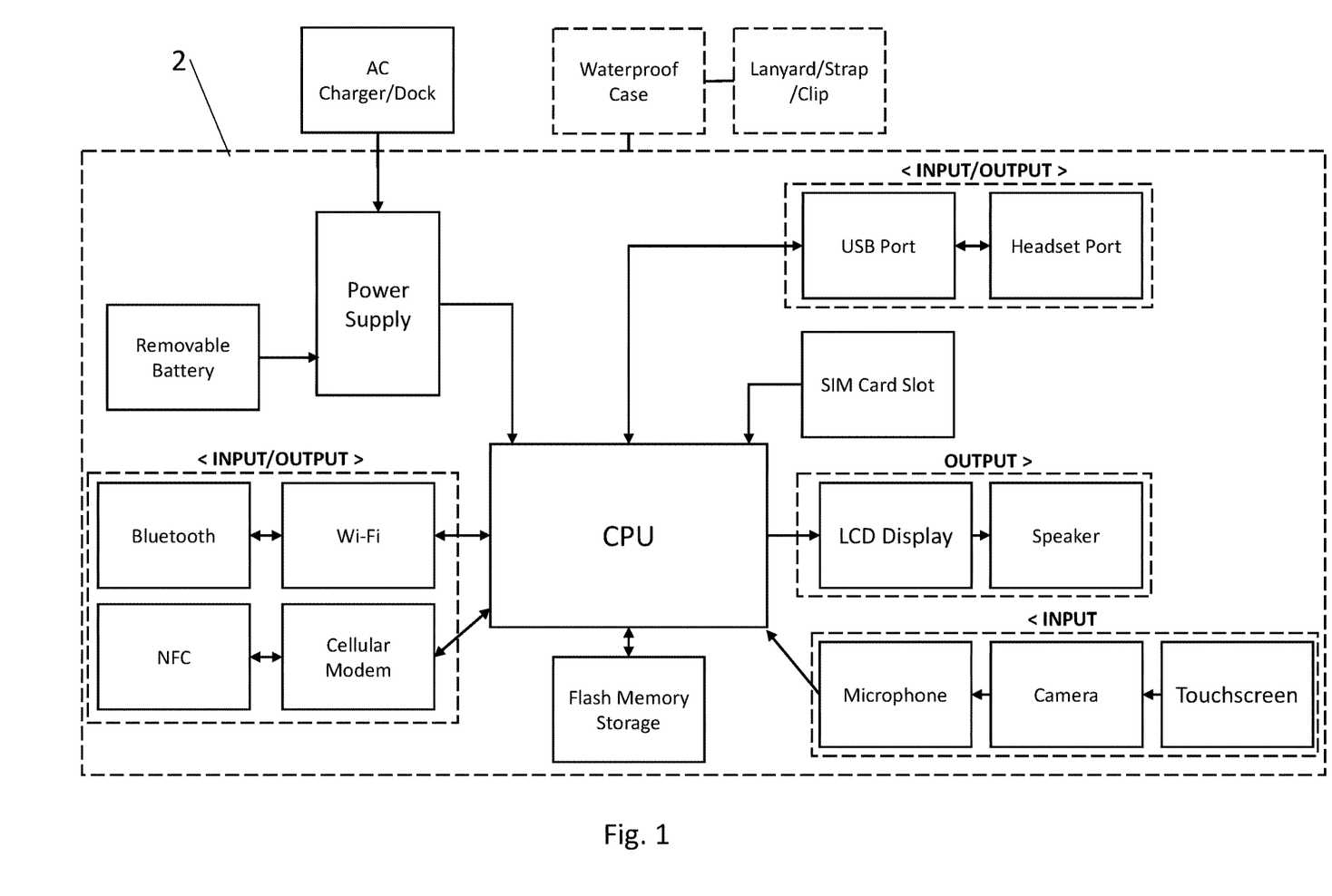
FIG. 1 is a schematic block diagram of internal elements of an exemplary Media Therapy Device (MTD).
Figure 2:
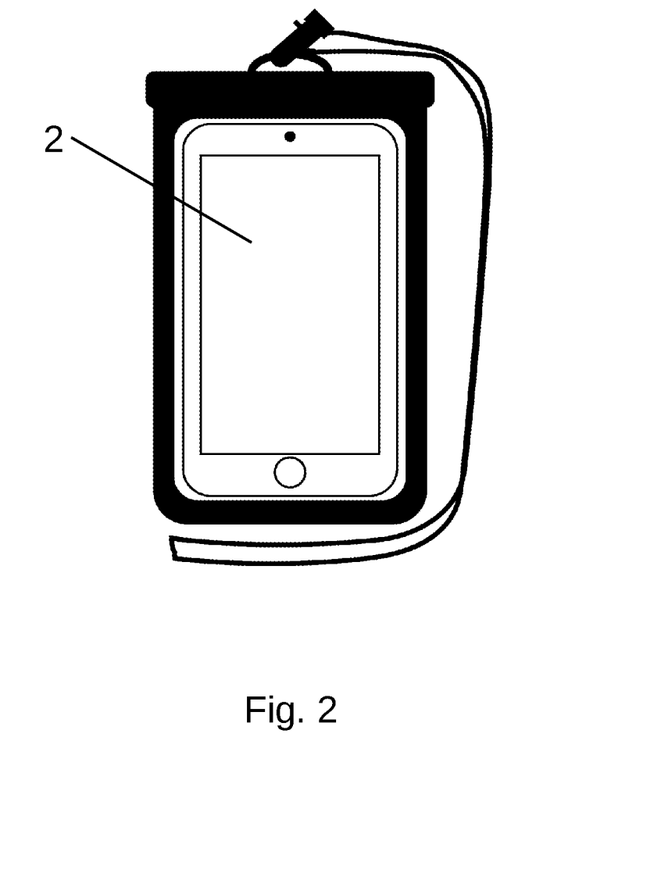
FIG. 2 is a front isometric view of the MTD of FIG. 1, demonstrating a protective cover/neck strap.
Figure 3:
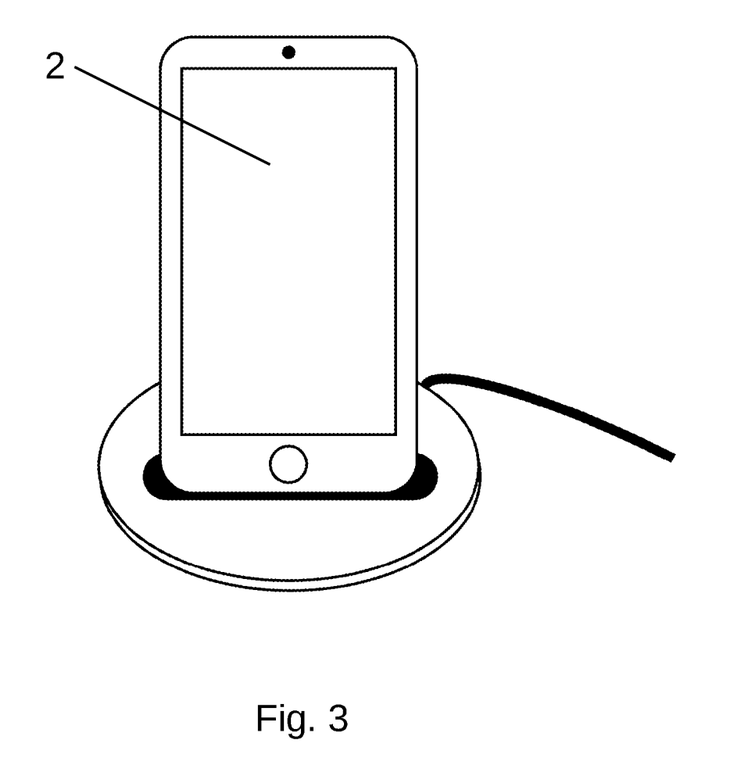
FIG. 3 is a front isometric view of the MTD of FIG. 1, seated in a power cradle.

As shown in FIGS. 1-3 an exemplary MTD includes a central processing unit, memory, battery/power supply, A/V input/output and communications functionality (see FIG. 1) in a rugged and compact form factor. One skilled in the art will appreciate such functionality is readily available in standardized and inexpensive embodiments of, for example Android or Apple, consumer cellular telephones and the like. As will be explained with respect to system operation herein below, such cellular telephones can communicate utilizing local network and/or device to device communications (Wi-Fi, Bluetooth, NFC and the like) and as such do not need to utilize or require the complexity and/or expense of cellular telephone network registration/communications. The MTD may include protective cases, clips, straps, lanyards or the like to secure the MTD to an AD patient to be monitored (see FIG. 2). For maximum battery life, the MTD may be provided bedside with a mains power connection, such as a charge cradle (see FIG. 3).

Figure 4:
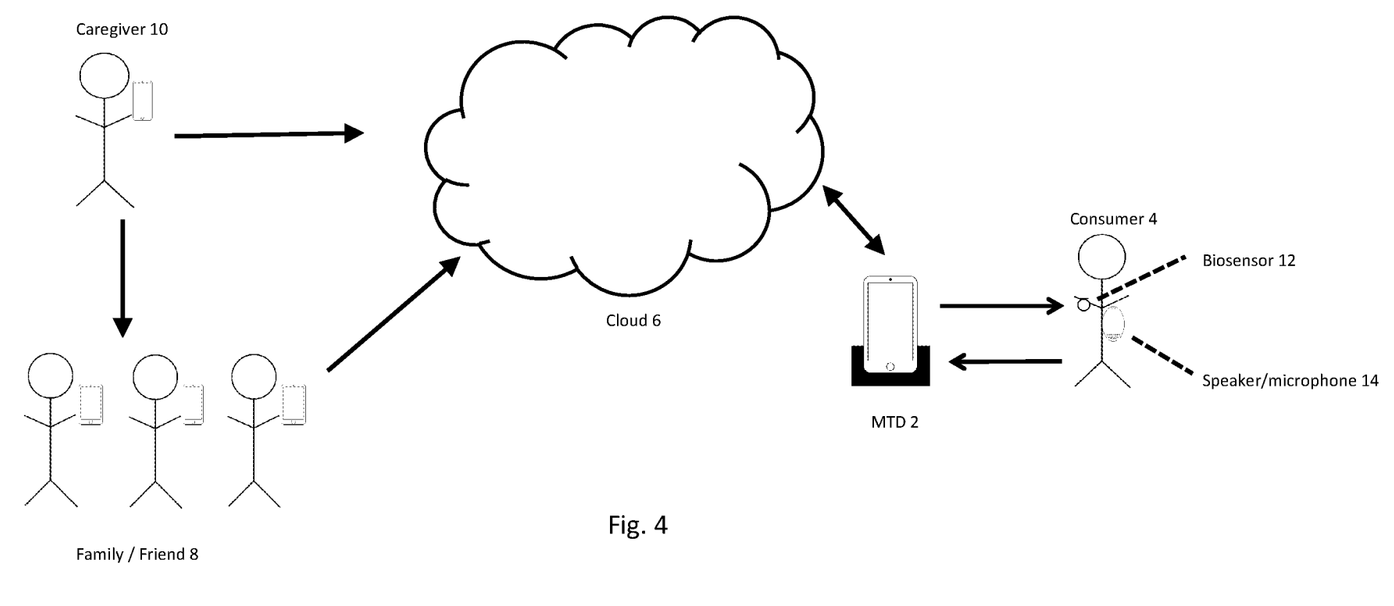
FIG. 4 is a schematic system diagram, demonstrating MTD configuration/management via cloud services.

The MTD 2 may include or be linked with separate biosensor(s) 12 and/or speakers/microphones 14 attached to each Consumer (see FIG. 4). While bedside, the MTD 2 may also be utilized as a master control unit that is coupled to simpler slave units that may be easier for the Consumer 4 to wear. Slave units may include speaker and microphone functionality as well as wired or wireless connections to further body worn sensors such as wrist band or the like pulse, respiration, blood pressure, Oxygen and/or temperature sensors.

MTD may also be utilized with further local devices provided with mains power connections, such as smart speakers, monitors or the like, significantly extending the battery life of the MTD by utilizing the smart speakers and/or monitors for the high power consumption task of providing audio and/or visual feedback at suitable volume as triggered by the rules of the local Consumer(s) MTD configuration.

Alternatively, these functionalities may be incorporated into a purpose built/dedicated MTD device, enabling optimization of features such as overall size, ruggedness, battery life and/or audio/visual output capacity (such as high volume for a sustained period).

In a system, as shown for example in FIG. 4, utilizing one or more MTD 2, for example one MTD per Consumer 4, to be monitored and/or one MTD/AD resident area zone to be monitored, a selected MTD 2 running a local "app" software package dedicated to the, for example AD patient, Consumer 4 monitoring/feedback protocols described herein may be monitored and/or configured via communications protocols such as Wi-Fi, Bluetooth or NFC. Further, the configuration and/or enablement of a specific MTD 2 may be entirely remote, linked through an available local network to one or more internet cloud servers and/or data storage resources (collectively referred to as the Cloud 6) offloading the data processing and storage requirements, improving cost efficiency and enabling cost efficient subscription management/income streams from large numbers of MTD provided to AD patient locations or the like anywhere internet communications are available around the world.

Alternatively, and/or additionally, local wireless configuration may be enabled, for example, via a smart phone application that can communicate with a central server that then connects to a selected MTD or directly with a specific local MTD. Similar to the ease with which an inexpensive cellular telephone may be utilized as the MTD, both Family/Friends 8 and local Caregivers 10 may efficiently interact with the Cloud 6 to issue/transmit instructions/feedback/invoicing/payments and or further media segments via their own computers and/or cellular telephones via modified "app" software linkable to the Cloud 6.

MTD audio and/or visual feedback may be configured with repetitive audio and/or visual messaging specific to a Consumer's needs, schedule and/or sensed emotional state. For example, messaging may include timely prompts of where the patient is, the date, to exercise, eat/drink, visit the bathroom, remind of upcoming events/visits, playing of personal messages from the patient's family/loved ones or specific music tracks known to be favored by the patient.

In particular, in use with Consumers with AD symptoms, it has been recognized that there is a significant benefit from a schedule that includes repetition of the same message, for example at 10 or 15 minute intervals, as a planned action or meeting approaches. This repetitive media therapy places the Consumer at ease where they would otherwise be suffering agitation from their lack of ability to form/retain short term memories of what they can expect to/have been advised will happen next. The ease of configuring a Consumers media play schedule via, for example a web page or app interface enables efficient application of a particular media/message with a message specific repetition interval which may include, for example, a tapering schedule and/or revision of the specific media to be played as a specific event approaches.

In addition, the messages may be determined by a professional Caregiver to target specific healthy behaviors (e.g., to counter potential dehydration, loved ones leave a message "Mom, it's Rick. Please take a drink of water now so that you stay healthy."). Because the messages are in a loved one's voice, they're shown to have a calming effect on agitated care recipients and the care recipients are more likely to heed the message or instruction that is in the form of a recognized family member's voice. Overall, this results in less stress for the Caregiver as well. During the COVID-19 pandemic, the use of the MTD has also proven effective in bridging the gap that exists between families and their loved ones due to pandemic isolation assisted living.

In addition, such prompts/messages may be selected from an available listing of prepared prompts/files or recorded and specifically assigned for a given patient, for example in a voice/by a person that may be recognizable by the patient. The networked aspect of an MTD configuration enables easy generation of new and/or daily specific audio and/or visual feedback, as well as tuning of repetition intervals of specific messages by Caregivers and/or family members from locations that may be entirely remote from the patient's location.

Confusion and/or frustration of AD Consumers may manifest in agitation/yelling episodes that can be sensed by an MTD monitoring a Consumer's audio environment. Responsive to such sensing, the MTD may be configured to vary the message, the time of the play, and/or frequency of play. Consumer specific audio may be selected according to rules configured (remotely if desired) beforehand, or the message/music may be configured according to a historical record/database of what message/music has worked better for a certain situation (I.e., anxiety at a certain time-of-day might show soothing music works best, yelling episodes might indicate a response from a family voice might work best, etc.). Consumer specific audio and/or video from a voice/video known to the patient can provide an immediate calming response, without the loved one needing to be local/present to the Consumer.

Further, as ongoing episodic data (for example where audio input detects ongoing distress) is collected such may be used to trigger escalating pre-configured responses up to the level of, for example, alerting a local Caregiver. Thereby improving local Caregiver responsiveness and enabling feedback that such triggered responses/interventions actually occur, for quality control of patient care.

Biometric sensing circuitry may be incorporated into the MTD or also networked from external devices in the patient's environment to the local MTD and/or back to a central server for assignment/action to the patient's data files/rules.

For example, inputs other than audio may be utilized. Accelerometers may be used to detect falls and/or GPS or LAN node connection data may be used as movement and/or location inputs that may become feedback triggers. Biometric data, such as heart and/or respiration rate, blood pressure, sweat level, body temperature and/or movement may also be collected as inputs for a rules episode trigger and as data for the effectiveness of a given input/response.

Further sensors may be selected from many existing attachable/wearable sensors which would communicate with/report to the MTD, for example via local communications protocols such as Bluetooth or the like, enabling customization of the parameters to be monitored according to a Consumer's particular situation/needs as these evolve during their ongoing therapy/disease progression.

Episodic data may be collected for further tuning of the rules for best response to future similar events. Third party software (such as ABAIT) can be linked to the data base to influence learning of the device messages from historical data (what works best, when, and in what situations) and frequency.

Further to sensing the patient's state/environment, the MTD may also accept direct commands from the Consumer and/or local Caregivers for a specific media file. In addition, the MTD/rules specific to an individual MTD may provide guide information to a Caregiver's device, such as an email, message or smart phone running a connected application, with patient specific data and/or suggestions as to how a local Caregiver may best respond to the current patient and/or this patient's sensed episode. Thereby, a loved one or paid Caregiver can receive real time Consumer specific advice for best practice care based upon a specific patient history/database.

Figure 5:
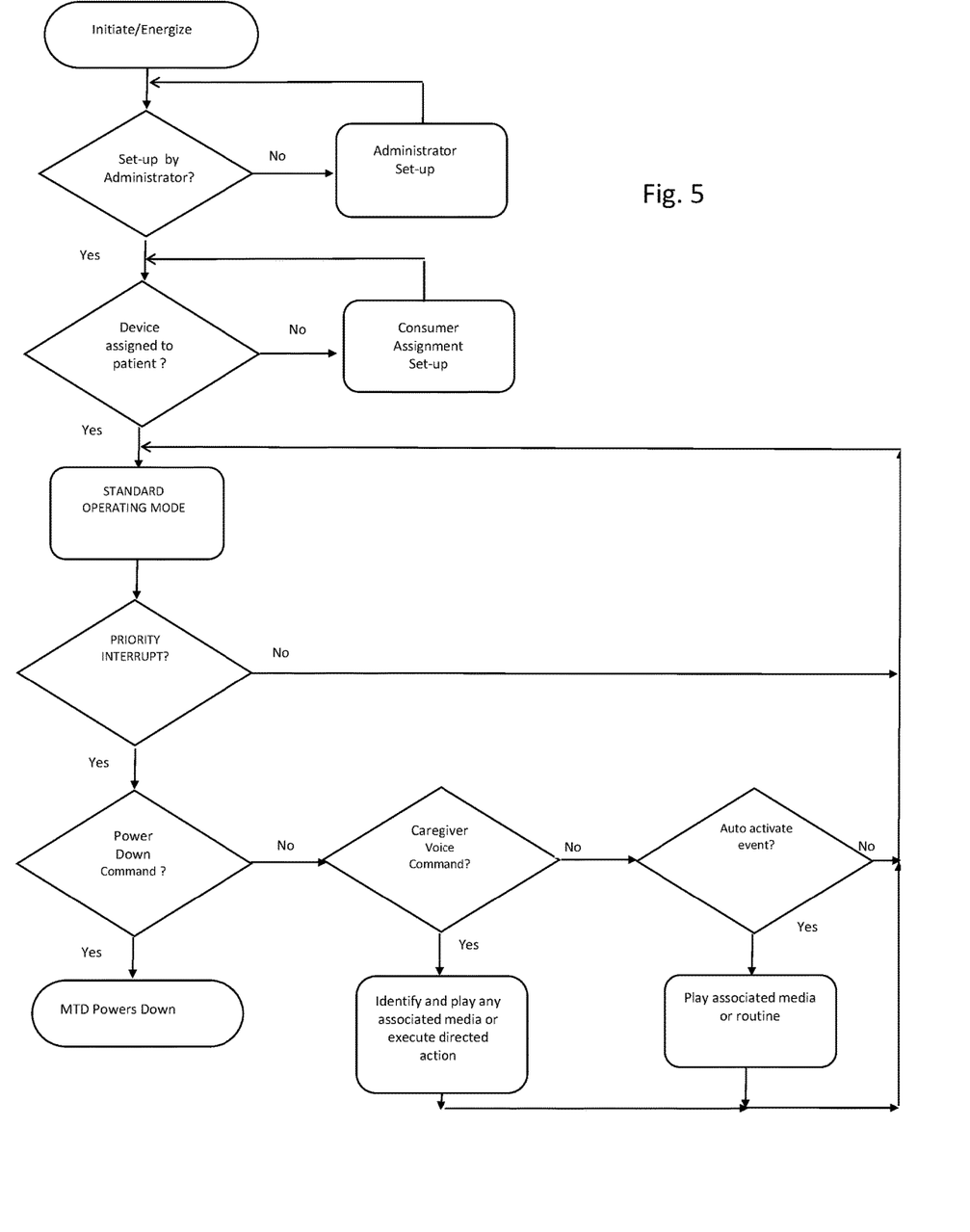
FIG. 5 is a schematic flow chart demonstrating initiation and steady state of therapy.

In use, as demonstrated for example in FIG. 5, upon initial power up, if the MTD has not been configured, an administrative set-up routine is performed, linking the MTD to a specific location's network connectivity and there through to the various Cloud administrative functions such as creating/verifying a service/cloud subscription. Further, if the MTD has not been assigned to a specific Consumer and/or if customization of the rules/media for the specific Consumer have not been made, these are configured/confirmed.

Once configured, the MTD will enter a Standard Operating Mode (SOM) according to the rules/media that have been configured for the MTD's assigned Consumer. Although an MTD in SOM is responsive to its assigned schedule and/or Consumer monitored event triggers, the SOM state may be interrupted by a range of priority interrupts, such as a power down command, a specific Caregiver voice command or an MTD out of the ordinary Auto-Activate Mode.

With respect to a power down command, these may be received, for example, manually at the MTD or administratively via the Cloud.

Figure 6:
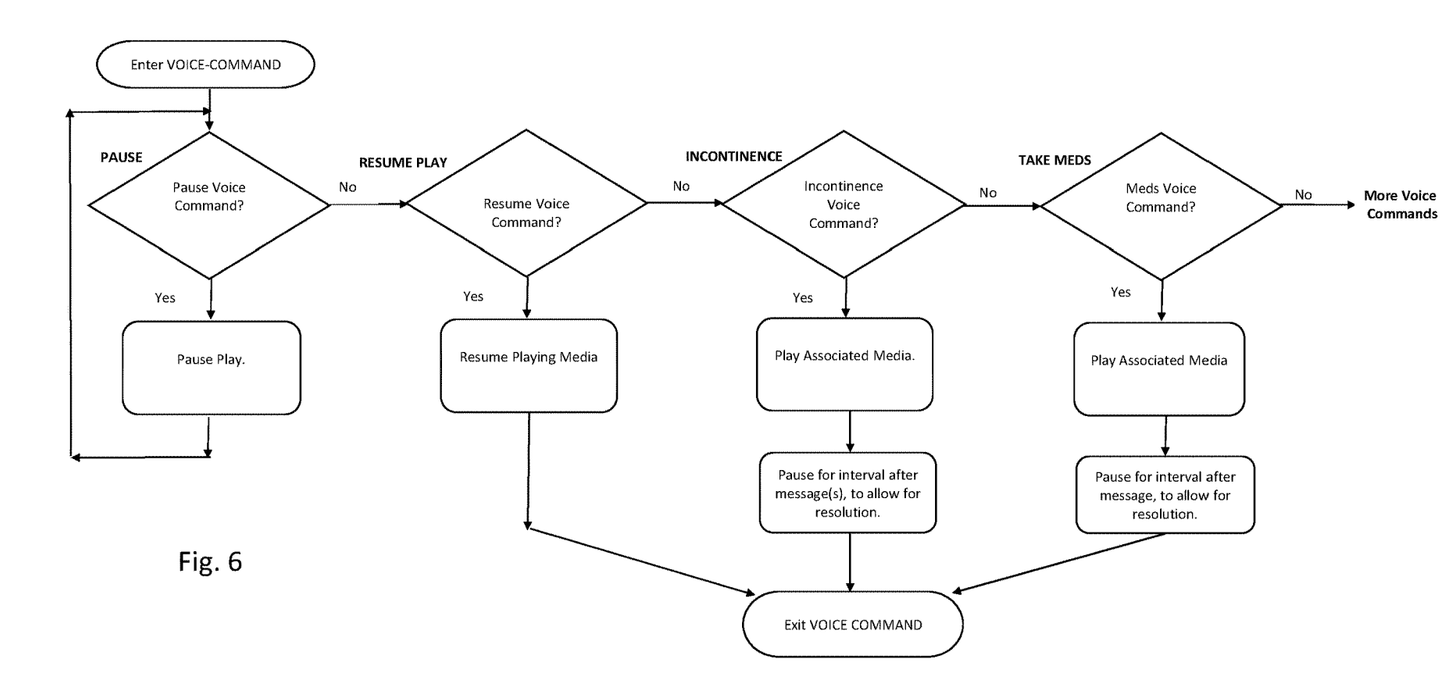
FIG. 6 is a schematic flow chart demonstrating Voice Command functions.

A Caregiver voice command, for example as demonstrated in FIG. 6, may be any of a range of voice commands (natural language voice spoken inputs) sensed by the MTD, such as a pause command that would pause the play of a media file so the Caregiver can have the Consumer's attention. The Pause command may stay active until removed by the Caregiver, for example by a Resume command or be based on a pre-configured timer or sub-command provided with the Pause command, such as "Pause for X minutes".

Voice commands may also be configured for routine/recurring consumer events. For example, incontinence may be a daily issue for the Consumer. An Incontinence voice command may interrupt whatever media may be playing, changing over to a specific incontinence media message from a Family member alerting the Consumer that the Caregiver is about to assist the Consumer to clean up. Similarly, a Meds voice command can initiate media message(s) that let the Consumer understand it is time to take medicines and that complying with such will help keep the Consumer healthy. Further voice commands may be similarly configured for other recurring activities which may occur "out of schedule" from time to time, such as napping, bathing, getting dressed, eating, visiting the bathroom or the like—assisting the Caregiver by letting the Consumer be guided in their tasks by a trusted family member's voice/via a context/activity specific media message even if it is not occurring according to the usual schedule.

Figure 7:
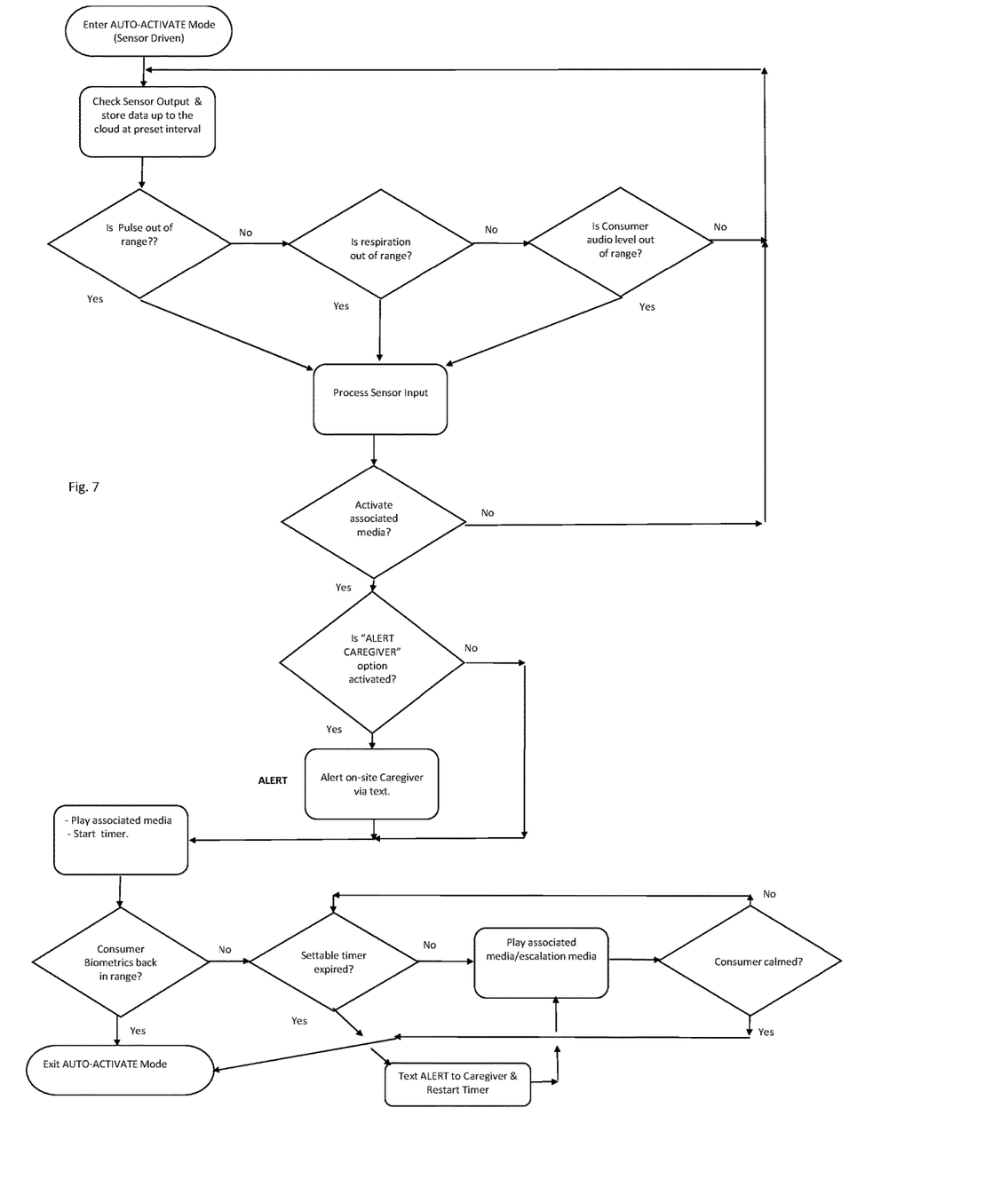
FIG. 7 is a schematic flow chart demonstrating Auto-Activate functions.

Auto Activate mode, as shown for example in FIG. 7, initiates a departure from regular SOM rules/media play upon detection of an out of range Consumer status. For example sensing that the Consumer's pulse, respiration and/or audio level (agitation/yelling associated with a louder voice) are out of range may be configured to play a pre-assigned "calming" media. Further such events may be configured to alert a Caregiver, for example via text. As an event progresses, if the Consumer is not sensed to have calmed within a set interval, a further pre-selected calming media may be played and/or an escalated alert may be sent for a Caregiver's attention. Once the Consumer is calmed, such may be recorded/reported and the SOM reinstated.

Figure 8:
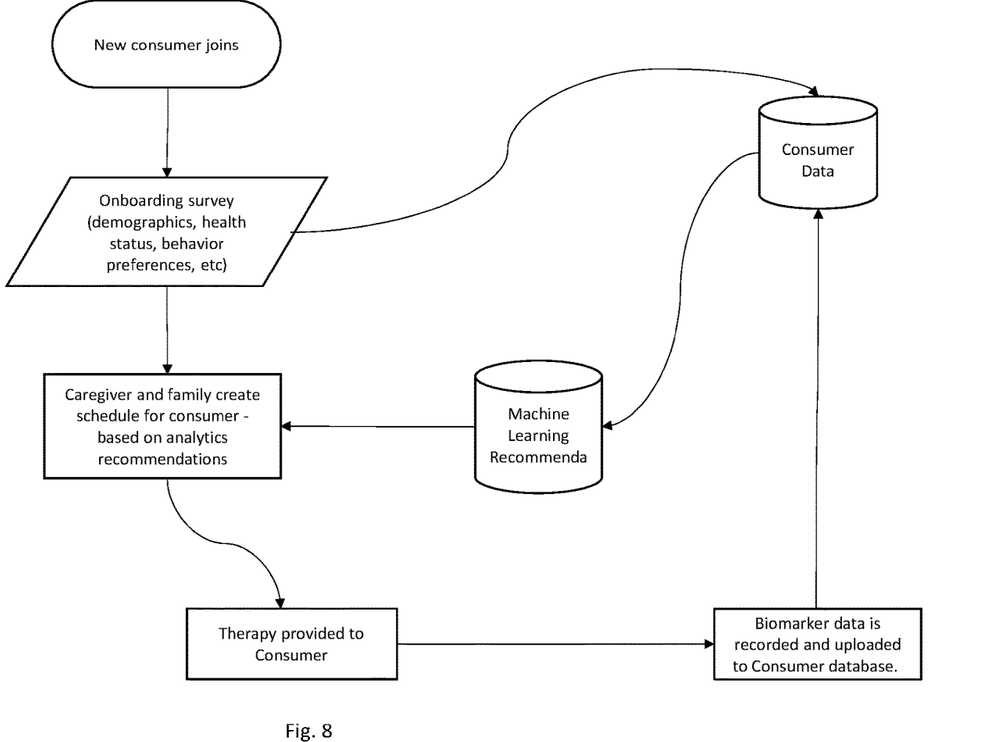
FIG. 8 is a schematic flow chart demonstrating cloud driven data mining incremental improvements for specific Consumer therapy protocols.

As shown in FIG. 8, system configuration, administration and feedback are enhanced by system operations via the cloud. For example, initial configuration may be via web survey pages/family member interview that query the Consumer's characteristic demographics (age, AD diagnoses, career, hobbies, culture and the like) which in turn allows selection of default media/schedule for event and/or scheduled play that the Consumer is more likely to recognize and enjoy, thereby improving the Consumer's quality of life and ease of care for the Caregiver. Once a base of information is generated, data mining with respect to prior therapy for similar Consumers may be applied to generate suggestions for media.

As the Consumer utilizes the system for their care, event data may be continually collected as feedback for tuning future care parameters to optimize the Consumer's experience. For example, data can indicate favorite/effective calming media, including recording artists and/or family members. Although a base set of Family member media recordings may be made, as care is ongoing further subject specific media may be requested via machine learning output or Caregiver specific request, to tune/provide continuous optimization of the Consumer's experience/quality of life.

One skilled in the art will appreciate that patient specific monitoring and/or intervention via the MTD enables improved Consumer care with reduced requirements and/or expense for actual physical local care of the patient.

| Table of Parts | |
|---|---|
| 2 | Media Therapy Device |
| 4 | Consumer |
| 6 | Cloud |
| 8 | Family/Friends |
| 10 | Caregiver |
| 12 | Biosensor |
| 14 | Speaker/microphone 14 |

Where in the foregoing description reference has been made to materials, ratios, integers or components having known equivalents then such equivalents are herein incorporated as if individually set forth.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus, methods, and illustrative examples shown and described. Accordingly, departures may be made from such details without departure from the spirit or scope of applicant's general inventive concept. Further, it is to be appreciated that improvements and/or modifications may be made thereto without departing from the scope or spirit of the present invention as defined by the following claims.

We claim:

1. A biometric status sensing media therapy system for the therapeutic care of a consumer, the system comprising:
a media therapy device provided with a central processing unit, audio and/or visual input/output and wireless communications;
the media therapy device in wireless communication with a cloud computing and data storage resource;
a collection of media files transmitted to the media therapy device from the cloud computing and data storage resource for play by the media therapy device according to a pre-configured collection of rules based upon a time schedule and a biometric status of the consumer wherein the biometric status of the consumer comprises an audio level proximate to the consumer; and
wherein the media therapy device is configured to interrupt the time schedule to play a pre-selected media file targeted to calm the consumer responsive to the audio level proximate to the consumer exceeding a threshold audio level indicating a louder voice or yelling of the consumer.

2. The system of claim 1, wherein the media files include messages from individuals known by the consumer.

3. The system of claim 2, wherein the individuals are family members of the consumer.

4. The system of claim 2, wherein the individuals known by the consumer may record a personalized media file and transfer it to the collection of media files via wireless communication.

5. The system of claim 1, wherein the biometric status of the consumer is a pulse rate or respiratory rate of the consumer.

6. The system of claim 1, wherein the rules include sensing of natural voice spoken inputs proximate the consumer.

7. The system of claim 1, wherein a rule initiated by a biometric status of the consumer includes an alert to a local Caregiver.

8. The system of claim 1, wherein the biometric status of the consumer is sensed by a slave unit wirelessly coupled to the media therapy device.

9. The system of claim 1, wherein the time schedule includes a selected repetition interval for the play of a specific media file.

10. A method for biometric status sensing media therapy of a consumer, comprising the steps of:
providing a system according to claim 1;
playing the media files according to the time schedule while monitoring the biometric status of the consumer; and
interrupting the time schedule to play a pre-selected media file targeted to calm the consumer if the biometric status of the consumer is detected to be out of range.

11. The method of claim 10, wherein the collection of media files includes media recordings made by individuals known to the consumer, the media recordings responsive to a care directive.

12. The method of claim 11, further including the step of generating one or more of the media recordings responsive to a request from a Caregiver responsible for the care of the Consumer.

13. The method of claim 11, further including the step of collecting the biometric status of the consumer over time as a feedback input of an effect of the playing of the media files upon the Consumer.

14. The method of claim 13, further including utilizing the feedback input to select media files for use in the collection of media files, weighted by an effect playing of the media files had upon the Consumer.

15. The method of claim 11, wherein a Caregiver may interrupt the schedule via a natural language spoken command proximate the Consumer.

16. The method of claim 15, wherein the natural language spoken command initiates play of a pre-selected media file.

17. The method of claim 11, wherein the biometric status of the Consumer is detected via a sensor in physical contact with the Consumer; the sensor in wireless communication with the media therapy device.

18. The method of claim 10, wherein the time schedule is provided with a message specific repetition interval for a specific media file.

19. The method of claim 18, wherein the time schedule includes a tapering repetition interval.

20. The method of claim 10, wherein interrupting the time schedule to play the pre-selected media file targeted to calm the consumer occurs responsive to real-time monitoring the biometric status of the consumer such that media files selected for playback are adjusted in real-time based on real-time monitoring the biometric status of the consumer.

* * * * *